(12) United States Patent
Inuki et al.

(10) Patent No.: US 6,298,877 B1
(45) Date of Patent: Oct. 9, 2001

(54) DISTRIBUTING VALVE DEVICE FOR HEAT ACCUMULATION TYPE COMBUSTION SYSTEM

(75) Inventors: Koji Inuki, Kawanishi; Hideo Yamaguchi, Yamatotakada, both of (JP)

(73) Assignee: Chugai Ro Co. Ltd., Osaka-Fu (JP)

( * ) Notice: Subject to any disclaimer, the term of this patent is extended or adjusted under 35 U.S.C. 154(b) by 0 days.

(21) Appl. No.: 09/249,156

(22) Filed: Feb. 12, 1999

(51) Int. Cl.$^7$ ................................................. F23G 7/06
(52) U.S. Cl. .................... 137/625.11; 137/311; 110/211; 165/9
(58) Field of Search ..................... 137/309, 311, 137/625.11; 165/4, 7, 8, 9, 9.3, 909, DIG. 18, DIG. 33, DIG. 39, DIG. 41; 110/211

(56) References Cited

U.S. PATENT DOCUMENTS

| | | | |
|---|---|---|---|
| 1,428,525 | * 9/1922 | Bergman | ........................... 137/311 X |
| 2,769,619 | * 11/1956 | Juhasz | ........................... 165/DIG. 18 |
| 3,191,666 | * 6/1965 | Brandt | ........................... 165/DIG. 39 |
| 3,664,413 | * 5/1972 | Bo | ........................... 165/4 |
| 3,666,001 | * 5/1972 | Johnson | ........................... 165/9 |
| 4,280,416 | * 7/1981 | Edgerton | ........................... 165/7 X |
| 4,669,531 | * 6/1987 | Conde | ........................... 165/4 |
| 5,016,547 | 5/1991 | Thomason . | |
| 5,529,113 | * 6/1996 | Borowy | ........................... 165/9 |
| 5,562,442 | * 10/1996 | Wilhelm | ........................... 110/211 X |
| 5,700,433 | * 12/1997 | Somary | ........................... 110/211 X |
| 5,950,707 | * 9/1999 | Kozacka et al. | ........................... 165/9 |

FOREIGN PATENT DOCUMENTS

| | | | |
|---|---|---|---|
| 0548630-A1 | 6/1993 | (EP) . | |
| 50-121831 | 9/1975 | (JP) . | |
| 0028692 | * 2/1991 | (JP) | ........................... 165/9 |
| 7-305824 | 11/1995 | (JP) . | |

* cited by examiner

Primary Examiner—John Rivell
Assistant Examiner—Meredith H. Schoenfeld
(74) Attorney, Agent, or Firm—Birch, Stewart, Kolasch & Birch, LLP

(57) ABSTRACT

A distributing valve device for a heat accumulation type combustion system comprising a stationary valve mounted on an underside of a housing having six or more passages defined by partition walls provided therein at predetermined intervals, and having heat accumulators arranged in the passages, the stationary valve having six or more openings formed therein at an equal interval in circumferential direction of the stationary valve which communicate with the respective passages, and a rotary valve disposed in opposed relation on the stationary valve and having an exhaust gas supply opening, a treated gas discharge opening, and a purge gas supply opening formed therein sequentially in this order and at predetermined intervals in a direction of rotation of the rotary valve, wherein a seal member is arranged on a surface of the stationary valve in opposed relation to the rotary valve such that the seal member surrounds the each opening of the stationary valve, and a closed portion defined between the adjacent openings of the rotary valve by making an area of the closed portion larger than an area surrounded by the seal member surrounding the each opening of the stationary valve.

3 Claims, 8 Drawing Sheets

DISTRIBUTING VALVE DEVICE FOR HEAT ACCUMULATION TYPE COMBUSTION SYSTEM

BACKGROUND OF THE INVENTION

1. Field of the Invention

The present invention relates to a distributing valve device for a heat accumulation type combustion system wherein exhaust gas containing a smelly substance, such as an organic solvent, is combusted and the organic solvent and other smelly substances are removed from the exhaust gas before the gas is discharged.

2. Description of the Prior Art

Conventionally, exhaust gas to be treated containing smelly substance (hereinafter referred to as merely "exhaust gas"), such as organic solvent etc., which is produced in a coat drying oven or the like, is treated in a heat accumulation type combustion system, and then the so treated gas is discharged outward.

Above mentioned heat accumulation type combustion system is well known through Japanese Patent Laid-Open Publication No. 7-305824(1995) and other relevant Publications. As schematically shown in FIGS. 7A to 10, the heat accumulation type combustion system includes a housing 1, a distributing valve device 10, and a feed/discharge device 15. The distributing valve device 10 consists of a stationary valve 11 and a rotary valve 12.

Within the housing 1, as shown in FIG. 7B, a plurality of passages 3 ($3a_1$, $3a_2$, $3a_3$, $3b$, $3c_1$, $3c_2$, $3c_3$, $3d$) defined by radially extending partition walls 2 provided at predetermined interval in a circumferential direction of the housing 1 are formed. In each passage 3, known heat accumulators 4, each comprised of ceramic particles or the like, are arranged and connected to a communicating space provided above the passage 3. In the communicating space, a combustion device 5 is disposed, which includes, for example, a heater and a burner, which constitute a combustion chamber 6.

The stationary valve 11, as shown in FIG. 8, is comprised of a plate-form member disposed at a bottom opening of the housing 1 and has openings 16 ($16a_1$, $16a_2$, $16a_3$, $16b$, $16c_1$, $16c_2$, $16c_3$, $16d$) corresponding to respective passages $3a_1$, $3a_2$, $3a_3$, $3b$, $3c_1$, $3c_2$, $3c_3$, $3d$.

The rotary valve 12, as shown in FIG. 9, is comprised of a plate-form member adapted to be rotated by a rotary shaft 12a, and has an opening 13a opposed to openings 16 of the stationary valve 11, for example, $16a_1$, $16a_2$, $16a_3$, and an opening 13c opposed to openings $16c_1$, $16c_2$, $16c_3$, and a purge gas supply opening 13b formed between openings 13a and 13c and upstream of the opening 13a in the direction of rotation of the rotary valve 12. In addition, a closed portion 13d is provided between the openings 13a and 13c and downstream of the opening 13a in the direction of the rotation of the rotary valve 12, where no opening is provided. For example, the opening 13a is used for supplying exhaust gas, and the opening 13c is used for discharging treated gas. Boundary portions of the openings 13a, 13b, 13c and of the closed portion 13d, and the outer periphery and inner periphery of the rotary valve 12 are fitted with a seal member 14 for preventing leakage of the exhaust gas and the treated gas from the clearance between the stationary valve 11 and the rotary valve 12 toward other opening.

According to the above described arrangement, the exhaust gas is supplied from a feeding port of a feed/discharge device 15 into the passages $3a_1$, $3a_2$, $3a_3$ through the opening 13a of the rotary valve 12 and the openings $16a_1$, $16a_2$, $16a_3$ of the stationary valve 11. The exhaust gas is guided from these passages into the combustion chamber 6, in which any organic solvent contained in the exhaust gas is combusted by the combustion device 5 such that the exhaust gas is heated to a temperature of 800 to 900° C. Subsequently, the exhaust gas is allowed to flow into the passages $3c_1$, $3c_2$, $3c_3$, and during the process of passing through the passages, the exhaust gas heats up the heat accumulators 4 within the passages and then, the exhaust gas itself becomes treated gas by being cooled. The treated gas is discharged from a discharge vent of the feed/discharge device 15 to a predetermined site through the openings $16c_1$, $16c_2$, $16c_3$ of the stationary valve 11 and the opening 13c of the rotary valve 12.

Furthermore, the rotary valve 12 is rotated intermittently or continuously in the direction shown by an arrow in FIG. 9, such that supply and discharge of the exhaust gas and the treated gas are carried out by sequentially changing the openings and passages through which the exhaust gas and the treated gas are respectively allowed to pass. In this way, the exhaust gas passes through the heat accumulators 4 which have been already heated by passage of hot treated-gas therethrough, whereby the exhaust gas is preheated and then, it is conducted into the combustion chamber 6.

In the rotary valve 12, the purge gas supply opening 13b and the closed portion 13d are disposed in opposed relation between the exhaust gas supply opening 13a and the treated gas discharge opening 13c, each opening being partitioned by the seal member 14. As shown in FIG. 8, each sector-shaped opening 16 of the stationary valve 11 has a central angle $\theta_2$, and a closed portion 17 defined between adjacent openings has a central angle $\theta_3$. As shown in FIG. 10, a sector-shaped closed portion 18 is formed between the purge gas supply opening 13b and the exhaust gas supply opening 13a of the rotary valve 12, and also between the purge gas supply opening 13b and the treated gas discharge opening 13c, the sector-shaped closed portion 18 surrounded by the seal member 14 having a central angle $\theta_3$ and the seal member 14 surrounding the purge gas supply opening 13b having a central angle $\theta_1$. In this case, the relation between respective angles are defined to be $\theta_2 \geq \theta_1$ and $\theta_3 \geq \theta_2$; therefore, at least one of the two sea 14 which partition adjacent openings of the rotary valve 12 from each other is always present in the closed portion 17 of the stationary valve 11. Therefore, at the openings 16 of the stationary valve 11, there is no possibility of the exhaust gas going into mixture with the treated gas, or the exhaust gas going into mixture with the purge gas, or the treated gas going into mixture with the purge gas. Furthermore, clean air is supplied from the purge gas supply opening 13b by a means not shown and, along with the clean air, residual exhaust gas at previous stage of treatment which remains within the heat accumulators 4 is conducted into the combustion chamber 6 and combusted therein. Therefore, when the treated gas is discharged later by being caused to pass through the heat accumulators 4, untreated exhaust gas is prevented from being discharged together with the treated gas.

In above described conventional distributing valve device of the heat-accumulation type combustion system, the relation between the opening 16 and the closed portion 17 of the stationary valve 11 is limited to be $\theta_3 \geq \theta_2$; therefore, for example, an area of the opening 16a of the stationary valve 11 cannot be made to be not less than 50% of an area surrounded by the seal member 14. Therefore, considerable pressure loss occurs at the time of gas supply or discharge, and this poses a problem that size enlargement is required with respect to the blower etc..

Another problem is that if an attempt is made to meet the relation of $\theta_3<\theta_2$ between the central angle $\theta_2$ of the opening 16 and the central angle $\theta_3$ of the closed portion 17 in the stationary valve 11 so as to make the area of the opening of the stationary valve 11 greater than 50% of above-mentioned area, the central angle $\theta_2$ of the opening 16 of the stationary valve 11 becomes larger than the central angle $\theta_3$ of closed portion 18 of the rotary valve 12 since the central angel $\theta_3$ of closed portion 18 of the rotary valve 12 is also $\theta_3$, as shown in FIG. 11. As a result, the exhaust gas supply opening 13a and the purge gas supply opening 13b are both present within the opening 16, resulting in insufficient purge of residual exhaust gas in the passage 3 within the housing 1. Therefore, the exhaust gas remains in the passage 3 and such exhaust gas residue thereafter becomes mixed with the treated gas as the treated gas is discharged through the passage 3, with the result that smelly substances, such as organic solvent, are diffused into the atmosphere.

Further, since the seal member 14 is conventionally provided on the rotary valve 12, frequent contacts between the seal member 14 and the opening 16 occur. In addition, as shown in FIG. 12, fragments 8 or the like of the heat accumulator 4 within the housing 1 are accumulated on the upper surface of the rotary valve 12. Therefore, the seal member 14 is subject to considerable damage so that exchange of the seal member 14 for new one is urged frequently for maintaining hermetic sealing.

SUMMARY OF THE INVENTION

The present invention has been made in view of the above mentioned problems of the prior art and, therefore, it is an object of the invention to provide a distributing valve device for a heat accumulation type combustion system wherein openings of the stationary valve disposed on an underside of a housing have an enlarged area such that pressure loss can be reduced, and wherein the possibility of seal members being damaged is reduced so that the seal members can retain the hermetic characteristic thereof for long term.

According to one aspect of the invention, in a distributing valve device for a heat accumulation type combustion system comprising a stationary valve mounted on an underside of a housing having six or more passages defined by partition walls provided therein at predetermined intervals, and having heat accumulators arranged in the passages, the stationary valve having six or more openings formed therein at an equal interval in circumferential direction of the stationary valve which communicate with the respective passages, and a rotary valve disposed in opposed relation to the stationary valve and having an exhaust gas supply opening, a treated gas discharge opening, and a purge gas supply opening formed therein sequentially in this order and at predetermined intervals in a direction of rotation of the rotary valve, wherein a seal member is arranged on a surface of the stationary valve in opposed relation to the rotary valve and in such a way as to surround the each opening of the stationary valve, and a closed portion defined between the adjacent openings of the rotary valve, an area of the closed portion being larger than an area surrounded by the seal member surrounding the each opening of the stationary valve.

According to another aspect of the invention, in a distributing valve device for a heat accumulation type combustion system comprising a stationary valve mounted on an underside of a housing having six or more passages defined by partition walls provided therein at predetermined intervals, and having heat accumulators arranged in the passages, the stationary valve having six or more openings formed therein at an equal interval in circumferential direction of the stationary valve which communicate with the respective passages, and a rotary valve disposed in opposed relation to the stationary valve and having an exhaust gas supply opening, a treated gas discharge opening, and a purge gas supply opening formed therein sequentially in this order and at predetermined intervals in a direction of rotation of the rotary valve, wherein an area of a closed portion defined between the adjacent openings of the rotary valve is larger than an area of the each opening of the stationary valve, wherein a seal member is arranged substantially all over the surface of the closed portions of the rotary valve opposed to the stationary valve such that the seal member surrounds the each opening of the rotary valve and closes the opening of the stationary valve when the closed portion is positioned at the opening of the stationary valve.

BRIEF DESCRIPTION OF THE DRAWINGS

These and other objects and features of the present invention will become apparent from the following description taken in conjunction with the accompanying drawings in which.

DETAILED DESCRIPTION OF THE INVENTION

Preferred embodiments of the invention will now be described with reference to the accompanying drawings.

Figure 1:
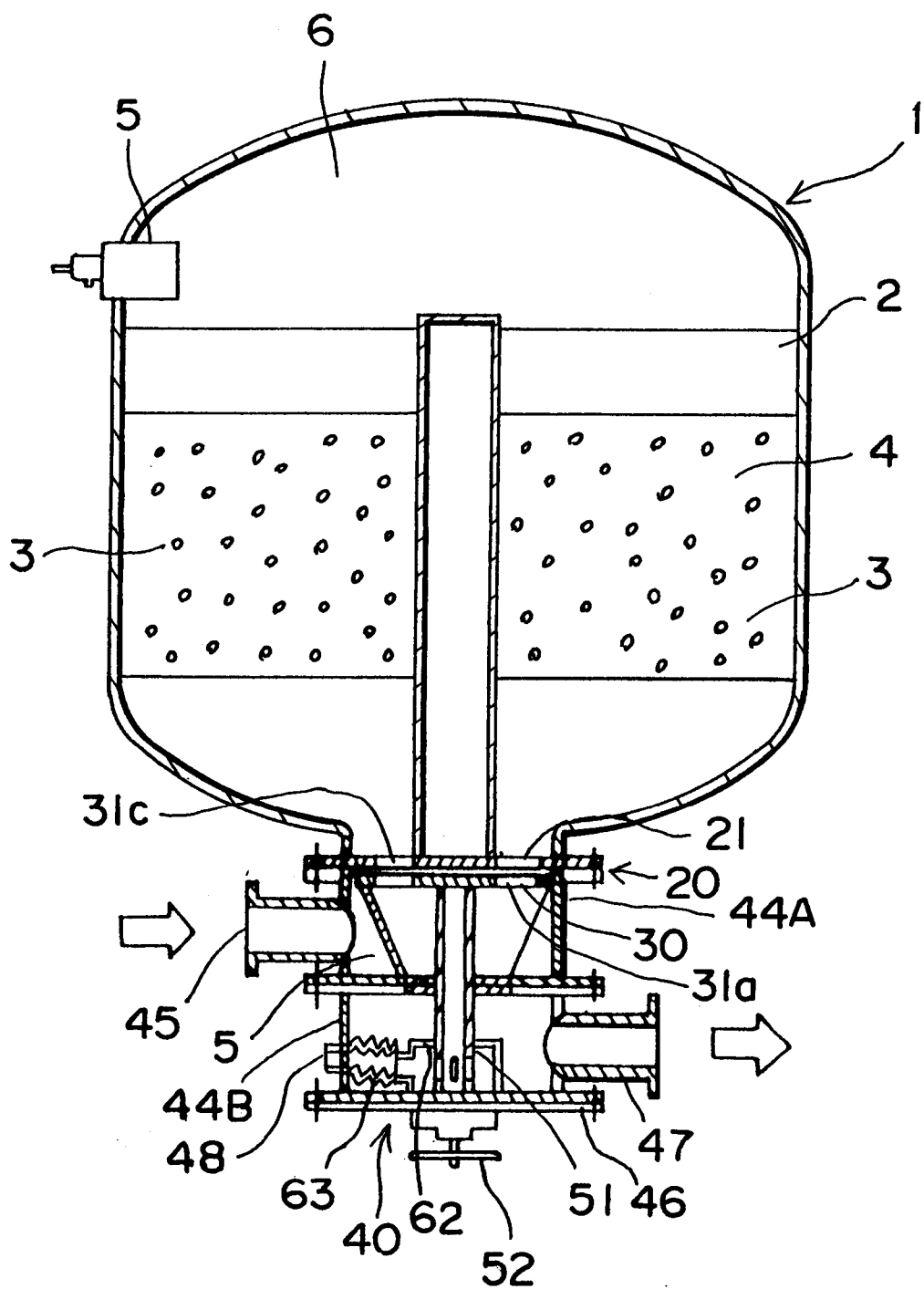
FIG. 1 is a schematic view in section showing a heat accumulation type combustion system including a distributing valve device according to a first embodiment of the present invention.

In a first embodiment of the invention, as shown in FIG. 1, a distributing valve device 20 of the heat accumulation type combustion system comprises a stationary valve 21 to be mounted to the bottom opening of the housing 1 and a rotary valve 30 disposed in opposed relation to the stationary valve 21, as in the case of the prior art. It is noted in this connection that the housing 1 has the same construction as the conventional one, except that the number of the passages 3 is different from that of the conventional one.

Figure 2A:
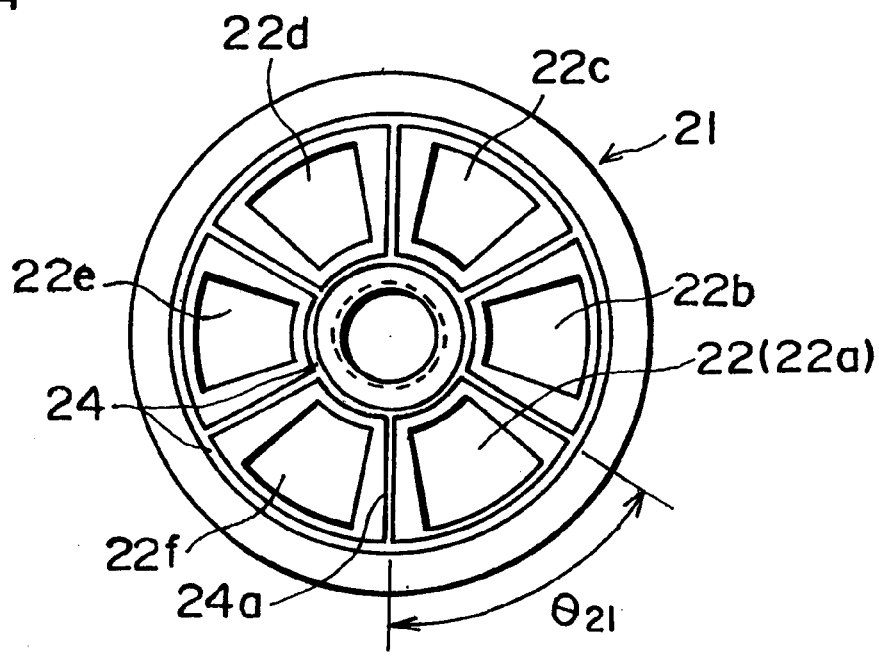
FIG. 2A is a plan view of a stationary valve shown in FIG. 1.
Figure 2B:
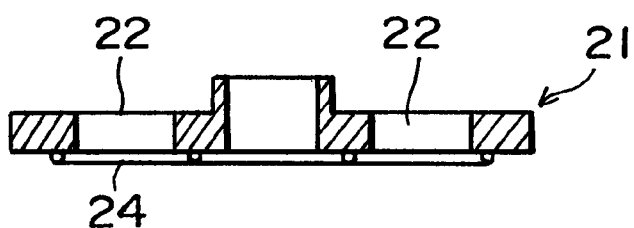
FIG. 2B is a sectional view of a stationary valve shown in FIG. 2A.
Figure 3:
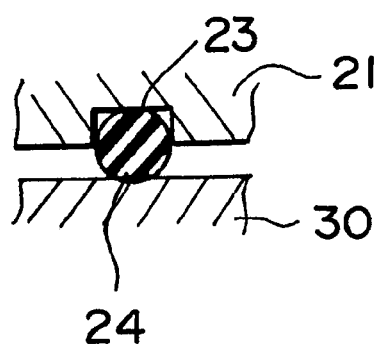
FIG. 3 is a fragmentary sectional view showing a mounted seal member.

The stationary valve 21, as shown in FIGS. 2A and 2B, has a disc-like configuration and includes openings 22 ($22a$, $22b$, $22c$, $22d$, $22e$, $22f$) arranged at an equal interval in corresponding relation to the passages 3 provided in the interior of the housing 1. As shown in FIG. 3, a groove 23 is provided around the openings 22, and a seal member 24 comprised of expanded rubber coated with fluorine resin is fitted in the groove 23, with its tip portion held in somewhat outwardly projecting condition. For the purpose of pressure loss reduction, the area of each of the openings 22 is not less than 50%, preferably not less than 90%, of the area surrounded by the seal member 24.

Figure 4A:
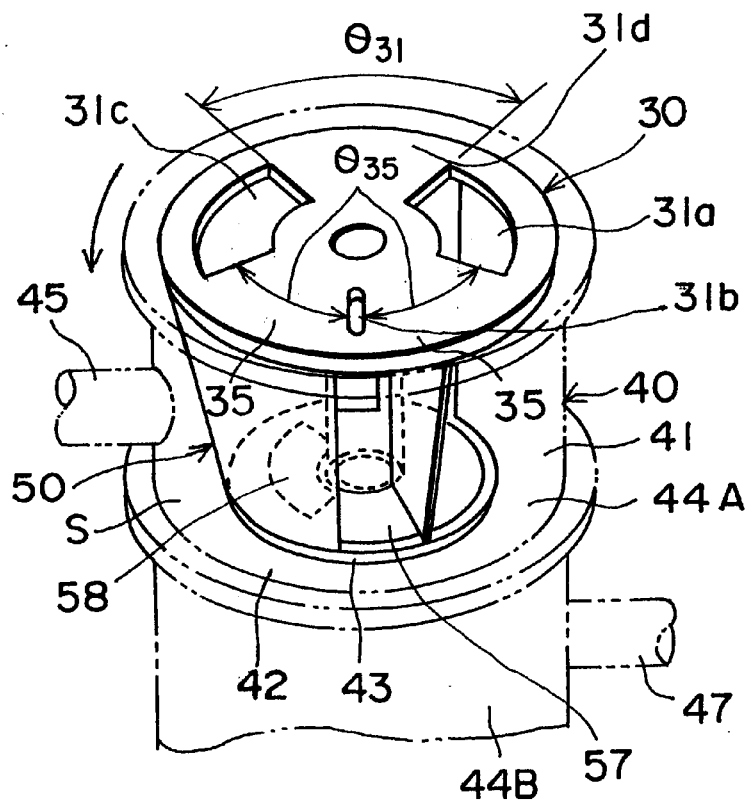
FIG. 4A is a perspective view showing the relation between a rotary valve and a feed/discharge device.
Figure 5:
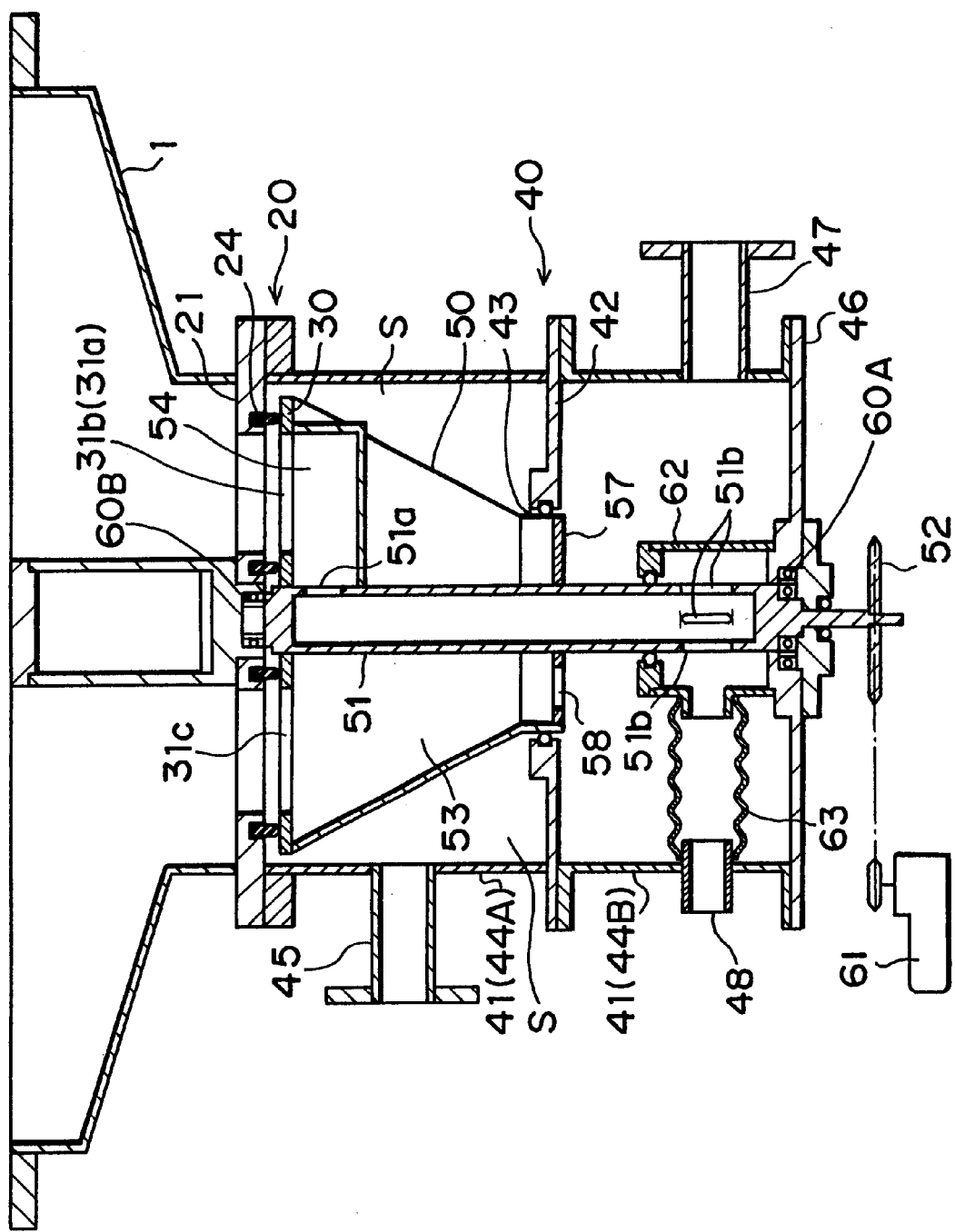
FIG. 5 is a sectional view showing the distributing valve device in assembled condition.

The rotary valve 30, as shown in FIGS. 4A and 5, has a disc-like configuration and includes, for example, an exhaust gas supply opening $31a$ communicating with an opening $22a$ of the stationary valve 21, a treated gas discharge opening $31c$ communicating with an opening $22e$ of the stationary valve 21, and a purge gas supply opening $31b$ provided between the two openings $31a$ and $31c$. In addition, between the exhaust gas supply opening $31a$ and the treated gas discharge opening $31c$, a closed portion $31d$ having no opening is provided, by which serves to partition the openings $31a$ and $31c$ from each other. Similarly, closed portions 35, 35 are provided respectively between the purge gas supply opening $31b$ and the exhaust gas supply opening $31a$, and between the purge gas supply opening $31b$ and the treated gas discharge opening $31c$ for partitioning the adjacent openings, respectively.

Each of the closed portions $31d$, 35, 35 is formed so as to be larger than the area defined by the seal member 24 surrounding one opening (e.g., $22a$) of the stationary valve 21. More specifically, as shown in FIGS. 2A and 4A, where the central angle of the seal member 24 surrounding one opening 22 of the stationary valve 21 is $\theta_{21}$, and respective central angles of the closed portions $31d$ and 35 of the rotary valve 30 are $\theta_{31}$ and $\theta_{35}$, the closed portions $31d$ and 35 are formed so as to meet relations $\theta_{31} \geq \theta_{21}$ and $\theta_{35} \geq \theta_{21}$ (where, $\theta_{21}$ represents an angle of an inner side of the seal member 24).

As a result, a linear portion $24a$ of the seal member 24 present between adjacent openings of the stationary valve 21 is always present at the closed portions $31d$ and 35 of the rotary valve 30. Therefore, there is no possibility of the exhaust gas, the treated gas, and the purge gas being mixed together at any one of the openings. Furthermore, as mentioned above, the openings $31a$, $31b$ and $31c$ of the rotary valve 30 are partitioned by the seal member 24 provided on the stationary valve 21, and thus it becomes possible to set an area of the opening 22 of the stationary valve 21 as desired within the scope of the area surrounded by the seal member 24. The area of the opening 22 is not less than 50%, preferably not less than 90%, of an area surrounded by the seal member 24.

On an upper surface of a rotor 50, i.e., a constituent member of a feed/discharge device 40 described hereinafter, the rotary valve 30 is mounted, which is able to slidably rotate relative to the stationary valve 21.

As shown in FIG. 5, the feed/discharge device 40 comprises a casing 41 and the rotor 50. The casing 41 has a generally cylindrical configuration and is partitioned at its middle portion by a partition plate 42 having a circular opening 43 at the center thereof so as to define an upper casing 44A and a lower casing 44B.

The upper casing 44A is fixed to the stationary valve 21 mounted on the bottom portion of the housing 1 and has a exhaust gas supply pipe 45. The lower casing 44B is provided with a treated gas discharge pipe 47 and a purge gas supply pipe 48, and is closed at its bottom portion by a lower cover 46.

Figure 4B:
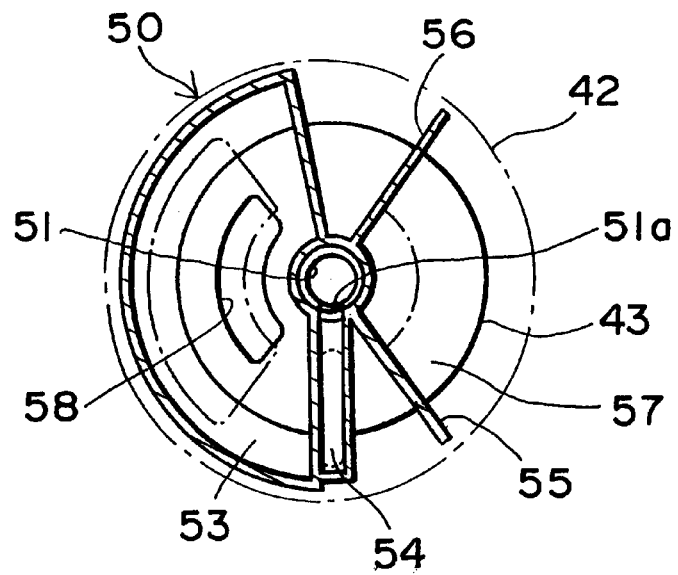
FIG. 4B is a sectional view of a rotor shown in FIG. 4A.

The rotor 50 is supported by a hollow shaft 51 which is supported by bearings 60A, 60B mounted respectively on the lower cover 46 of the lower casings 44B and the stationary valve 21. The upper end and the lower end of the hollow shaft 51 are closed. The rotor 50 is provided rotatably by a drive means 61 through a pulley 52 provided at the lower end of the hollow shaft 51. Further, the rotor 50 is disposed in a position above the hollow shaft 51 so as to be positioned within the upper casing 44A. In addition, as shown in FIG. 4B, the rotor 50, when viewed in transverse cross section, comprises a treated gas discharge space 53 having a sector shape, a rectangular purge gas supply space 54 adjacent to the treated gas discharge space 53, support plates 55 and 56 spaced a predetermined distance from each other for supporting the rotary valve 30. The spaces 53, 54 and the support plates 55, 56 are fixed to a bottom plate 57 mounted on the hollow shaft 51. The bottom plate 57 is slidably disposed in the circular opening 43 formed in the partition plate 42 of the casing 41 and closes the opening 43. The diameter of the rotor 50 becomes smaller in the downward direction such that a space S is formed between the rotor 50 and the lower portion of the upper casing 44A. The treated gas discharge space 53 communicates with the interior of the lower casing 44B through an opening 58 provided in the bottom plate 57.

As is apparent from FIGS. 4A and 4B, the exhaust gas supply opening $31a$ of the rotary valve 30 mounted on the upper surface of the rotor 50 communicates with a space between the support plates 55 and 56, the treated gas discharge opening $31c$ communicates with the treated gas discharge space 53, and the purge gas supply opening $31b$ communicates with the purge gas supply space 54, respectively.

A hollow rotary joint 62 is disposed above a bearing 60A supporting the lower end of the hollow shaft 51. The rotary joint 62 rotatably supports the lower end of the hollow shaft 51 and communicates with the purge gas supply pipe 48 through a bellows-like joint 63.

In the distributing valve device 20 of above described construction, the exhaust gas supplied from the exhaust gas supply pipe 45 to the upper casing 44A is allowed to pass through the exhaust gas supply opening $31a$ of the rotary valve 30 and the opening $22a$ of the stationary valve 21 from the exterior of the rotor 50 and is fed into the passage 3 of the housing 1. Subsequently, the exhaust gas passes through the heat accumulators 4 and then, enters the combustion chamber 6 in which the combustible content of the exhaust gas, such as organic solvent etc., is removed by combustion. As a result, the exhaust gas becomes hot treated gas. In the course of its flow through other passage 3, the treated gas heats up the heat accumulators 4, while the treated gas itself is cooled. The treated gas then reaches the treated gas discharge space 53 through the opening $22e$ of the stationary valve 21 and treated gas discharge opening $31c$ of rotary valve 30. Furthermore, the treated gas passes through the opening 58 provided on the bottom plate 57 and the lower casing 44B and then, is discharged from the treated gas discharge pipe 47.

Thereafter, at predetermined time intervals the hollow shaft 51 rotates by one pitch (which corresponds to one passage of the housing 1), and the exhaust gas is preheated by passing through the heat accumulators 4 in the passage 3 located downstream in the direction of rotation. In other words, the exhaust gas is preheated in the heat accumulator 4 heated at previous stage by the treated gas. Subsequently, the exhaust gas is combusted by the combustion device 5 in the combustion chamber 6. In this way, the above described operation is repeated. It is noted in the above connection that the hollow shaft 51 may be rotated continuously at predetermined velocity.

As shown in FIG. 5, air for purging is supplied in the hollow shaft 51 through its opening 51b and then, the air passes through an opening 51a of the hollow shaft 51 and the purge gas supply space 54 and the purge gas supply opening 31b. As a result, the air is fed to a passage in the housing 1 positioned upstream, in the direction of rotation of the rotary valve 30, of a passage in the housing 1 in which the exhaust gas is supplied. Subsequently, the purging air, together with the exhaust gas remaining in the passage at the previous stage, is supplied to the combustion chamber 6 in which organic solvent contained in the exhaust gas is combusted, whereby the exhaust gas is prevented from inclusion into the treated gas to be discharged at the next stage. The rotary valve 30 is provided with the closed portions 31d and 35, and the seal member 24 of the stationary valve 21 is always present at the closed portions 31d and 35. Therefore, at these portions, the treated gas and the exhaust gas can be prevented from being mixed together.

That is to say, as mentioned above, the closed portions 31d and 35 of the rotary valve 30 are larger in size than the area of one opening 22 surrounded by the seal member 24 of the stationary valve 21, so that the linear portions 24a of the seal member 24 are always present at the closed portions 31d and 35. Therefore, there is no possibility of the exhaust gas and the treated gas being mixed together in one opening. The area of opening 22 is not less than 50%, preferably not less than 90%, of the area surrounded by the seal member 24. Thus, it becomes possible to reduce the pressure loss.

The distribution of the exhaust gas to the passage 3 provided in the housing 1 is carried out through rotation of the rotary valve 30, and the seal member 24 is mounted to the stationary valve 21.

Therefore, one of the radially extending sides (i.e. linear portions 24a) of the seal member 24 comes into pressing contact with the peripheral edge of the openings of the rotary valve 30 six times during one rotation of the rotary valve 30. In contrast to this, if the seal member 24 is mounted on the rotary valve 30 as in the prior art system, the one of the radially extending sides of the seal member 24 comes into pressing contact with the peripheral edges of the openings of the stationary valve 21 twelve times in the case where the stationary valve 21 has 6 openings 22 as in the present embodiment. This means that in such a case the seal member 24 would be damaged twice as much. In the present embodiment, however, since the rotary valve 30 has the closed portions and, the openings 31 of the rotary valve 30 are smaller in number than the openings 22 in the stationary valve 21, the possibility of the seal member 24 being damaged is reduced.

Furthermore, since the seal member 24 is disposed on the stationary valve 21, fragments of the heat accumulator 4 or the like falling from the housing 1 are removed from the openings 31a, 31b, 31c of the rotary valve 30, so that the deposition of the fragments on the surface of the rotary valve 30 as in the prior art is prevented. Therefore, the seal member 24 is much less liable to be damaged. According to the present invention, therefore, high sealing effect can be maintained for long term.

Figure 6A:
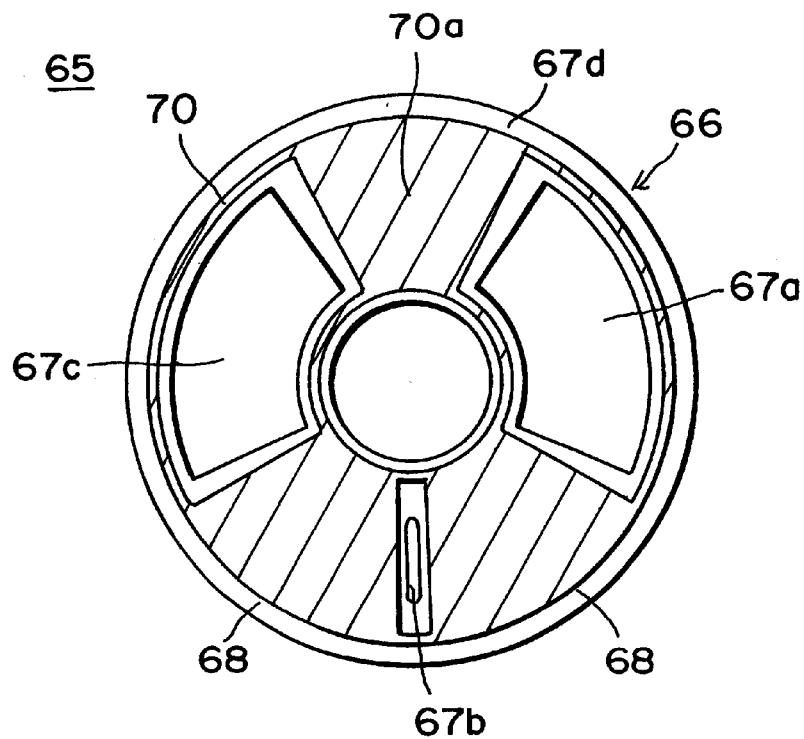
FIG. 6A is a plan view showing a rotary valve of a distributing valve device according to a second embodiment of the present invention.
Figure 6B:
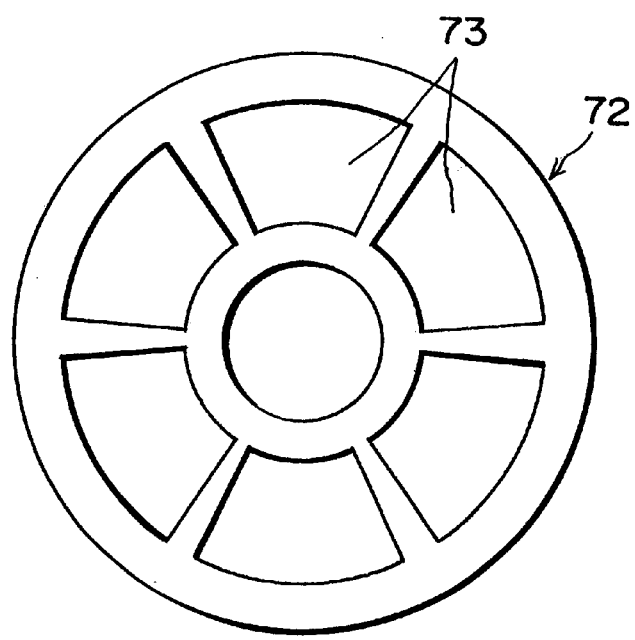
FIG. 6B is a bottom view of a stationary valve of the distributing valve device according to the second embodiment of the present invention.
Figure 7A:
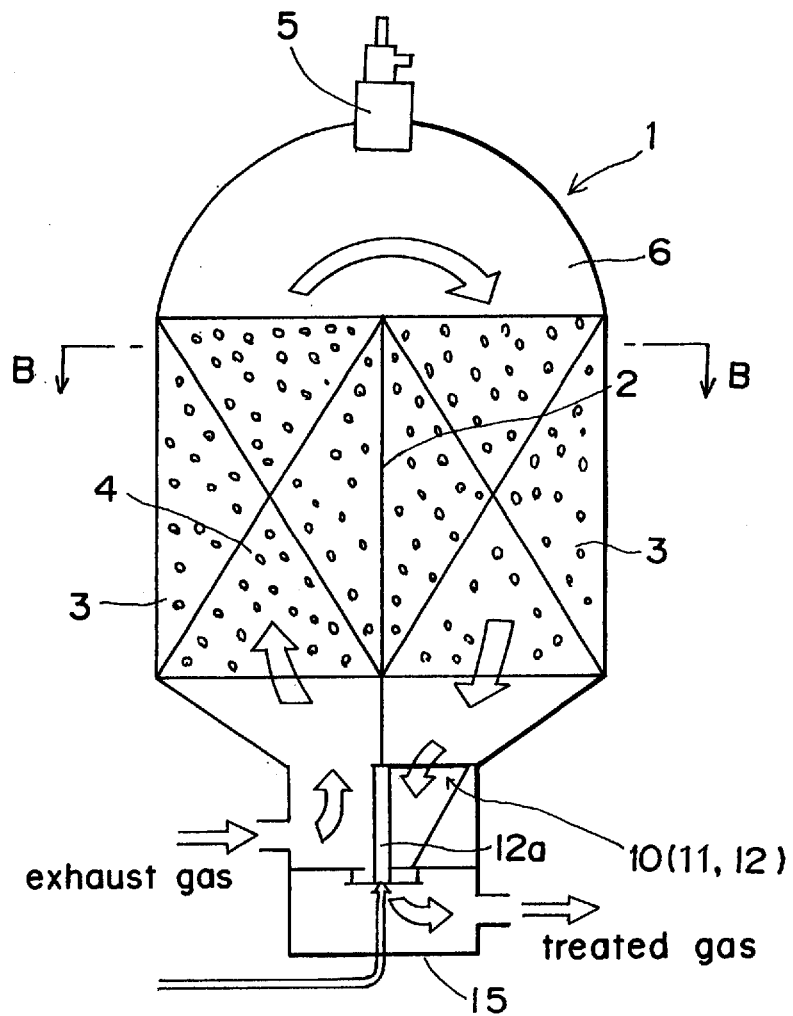
FIG. 7A is a schematic sectional view of a conventional heat accumulation type combustion system.
Figure 7B:
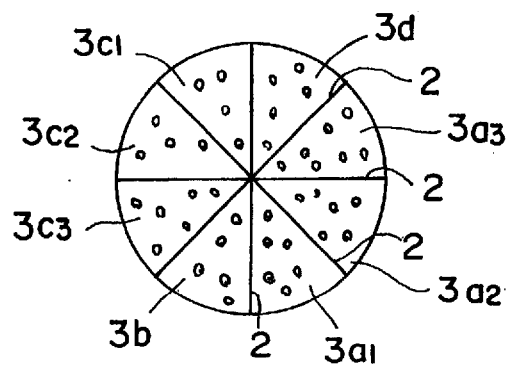
FIG. 7B shows a section taken along a line B—B in FIG. 7A.
Figure 8:
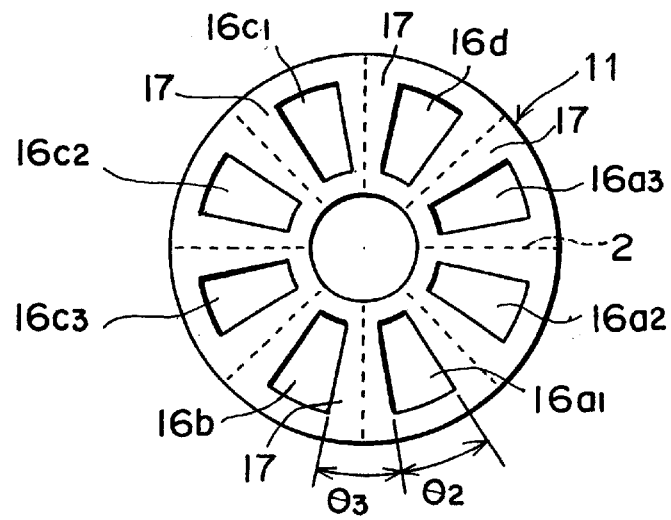
FIG. 8 is a bottom view of a stationary valve shown in FIG. 7.
Figure 9:
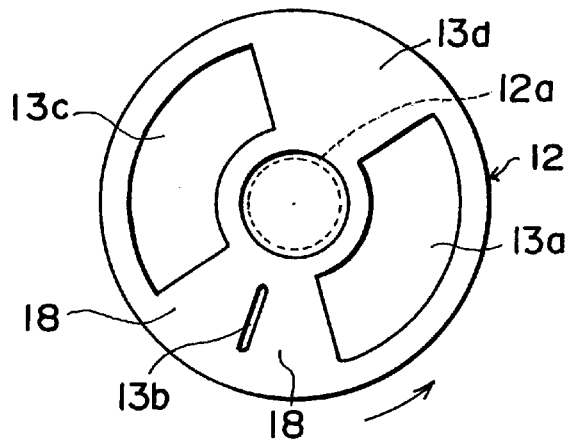
FIG. 9 is a plan view of a rotary valve shown in FIG. 7.
Figure 10:
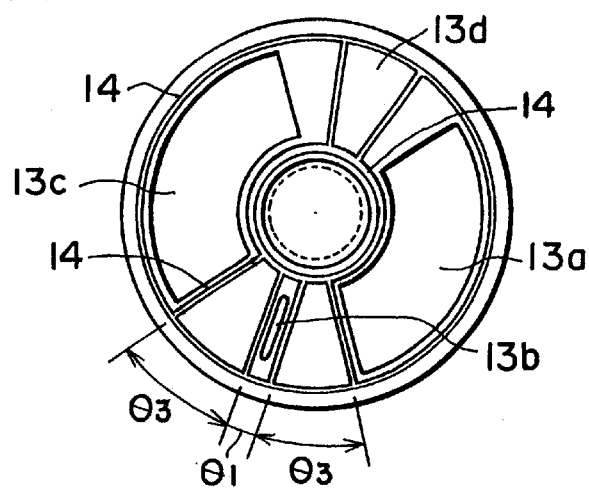
FIG. 10 is a plan view showing the rotary valve fitted with seal members.
Figure 11:
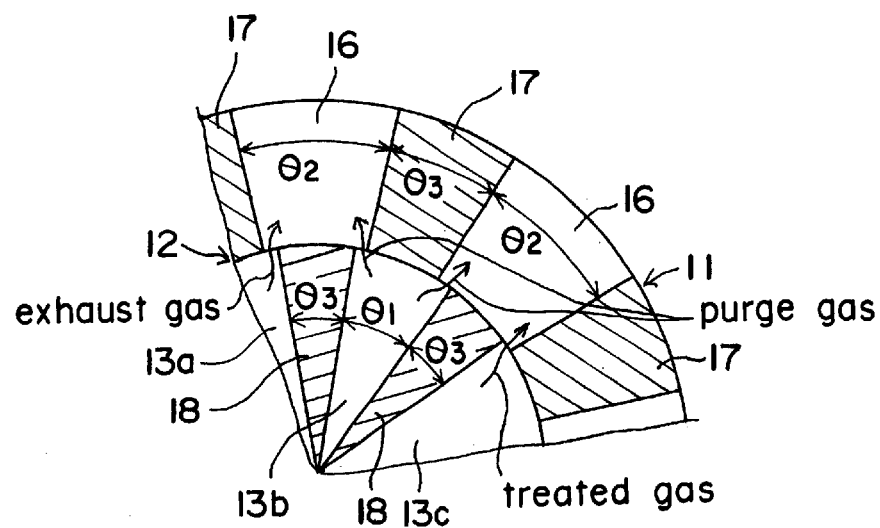
FIG. 11 is a schematic view for explaining problems as to the stationary valve shown in FIG. 8.
Figure 12:
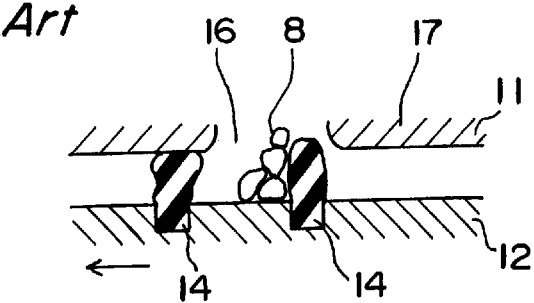
FIG. 12 is a schematic view for explaining another problem.

FIGS. 6A, 6B illustrate a distributing valve device 65 for heat accumulation type combustion system of a second embodiment. In this second embodiment, as shown, a seal member 70 is provided on the surface of a rotary valve 66 opposed to a stationary valve 72.

The rotary valve 66, as in the first embodiment, includes an exhaust gas supply opening 67a, a purge gas supply opening 67b, and a treated gas discharge opening 67c. Between the exhaust gas supply opening 67a and the treated gas discharge opening 67c, a closed portion 67d is provided, the area of which is larger than the area of each opening 73 of the stationary valve 72. Also, between the purge gas supply opening 67b and the exhaust gas supply opening 67a and between the purge gas supply opening 67b and the treated gas discharge opening 67c, closed portions 68, 68 are provided, each of which has an area larger than the area of opening 73 of the stationary valve 72.

The seal member 70 is so arranged as to enclose the openings 67a, 67b, 67c and to cover substantially all over the closed portions 67d, 68, 68. Thus, when the closed portions 67d, 68, 68 are positioned at the opening 73 of the stationary valve 72, the opening 73 can be closed.

By virtue of such arrangement, as in the first embodiment, it is now possible to supply the exhaust gas and discharge the treated gas, and thus to treat the organic solvent contained in the exhaust gas by combustion. Further, since the closed portion between adjacent openings 73, 73 of the stationary valve 72 is always present on the seal member 70, there is no possibility of the exhaust gas and the treated gas being mixed together. The area of the opening 73 of the stationary valve 72 is not less than 50%, preferably not less than 90%, of the area of the seal member 70a provided on the closed portion 67d, 68, 68. By virtue of this arrangement it becomes possible to reduce pressure loss. In addition, since the seal member 70 is arranged substantially all over the closed portion 67d, 68, 68, it becomes possible to cause the fragments of the heat accumulator 4 falling from the housing 1 to slide on the surface of the seal member 70a so as to fall from the opening 67a, 67b, 67c, whereby deposition of such fragments can be prevented.

In case that, in the second embodiment, a plurality of radially extending linear seal members are mounted on the closed portions 67d, 68, 68 of the rotary valve 66, such linear seal members should be disposed at narrower intervals than the width of the closed portion position ed between adjacent opening s of the stationary valve.

As is apparent from the above description, in the heat accumulation type combustion system of the present invention, by providing the seal member on the stationary valve for sealing the stationary valve and the rotary valve, the area of each opening of the stationary valve can be made to be not less than 50% of the area surrounded by the seal member and thus, it becomes possible to reduce pressure lose. Further, as compared with the prior art device in which the seal member is disposed on the rotary valve, the seal member in the present invention involves less frequent pressing contact with the edge of the opening and is not subject to deposition of the heat accumulator fragments or the like. In the present invention, therefore, the seal member is less liable to damage and can maintain high seal performance for long term, which results in reduced frequency of maintenance.

In the distributing valve device of the present invention wherein the seal member is provided on the rotary valve as well as on the stationary valve, the seal member is mounted on a substantially whole surface of the closed portion defined between adjacent openings, so that the area of each opening of the stationary valve can be made to be not less than 50% of the area surrounded by the seal member. This results in reduced pressure loss and provides for improvement with respect to problems of deposition of heat accumulator fragments and possible damage to the seal member.

What is claimed is:

1. A distributing valve device for a heat accumulation type combustion system comprising:

a stationary valve mounted on an underside of a housing having six or more passages defined by partition walls provided therein at predetermined intervals, and having heat accumulators arranged in the passages, the stationary valve having six or more openings formed therein at equal intervals in a circumferential direction of the stationary valve which communicate with the respective passages; and a rotary valve disposed in opposed relation to the stationary valve and having an exhaust gas supply opening, a treated gas discharge opening, and a purge gas supply opening formed therein sequentially in this order and at predetermined intervals in a direction of rotation of the rotary valve;

wherein said stationary valve includes a groove surrounding each opening of the stationary valve, and wherein a seal member is arranged in said groove and projects from a surface of the stationary valve to contact the rotary valve such that the seal member surrounds each opening of the stationary valve, and an area of a closed portion defined between the adjacent openings of the rotary valve is larger than an area surrounded by the seal member surrounding each opening of the stationary valve.

2. A distributing valve device for a heat accumulation type combustion system comprising:

a stationary valve mounted on an underside of a housing having six or more passages defined by partition walls provided therein at predetermined intervals, and having heat accumulators arranged in the passages, the stationary valve having six or more openings formed therein at equal intervals in a circumferential direction of the stationary valve which communicate with the respective passages; and a rotary valve disposed in opposed relation to the stationary valve and having an exhaust gas supply opening, a treated gas discharge opening, and a purge gas supply opening formed therein sequentially in this order and at predetermined intervals in a direction of rotation of the rotary valve;

wherein a seal member is arranged on a surface of the stationary valve in opposed relation to the rotary valve such that the seal member surrounds each opening of the stationary valve, and an area of a closed portion defined between the adjacent openings of the rotary valve is larger than an area surrounded by the seal member surrounding each opening of the stationary valve; and wherein said seal member includes a rubber material.

3. The distributing valve device according to claim 2, further comprising:

a fluorine resin coating applied to said rubber material.

* * * * *